United States Patent [19]

Katkocin et al.

[11] Patent Number: 4,536,477
[45] Date of Patent: Aug. 20, 1985

[54] THERMOSTABLE GLUCOAMYLASE AND METHOD FOR ITS PRODUCTION

[75] Inventors: Dennis M. Katkocin, Danbury, Conn.; Nancy S. Word, Woodridge; Shiow-Shong Yang, Downers Grove, both of Ill.

[73] Assignee: CPC International Inc., Englewood Cliffs, N.J.

[21] Appl. No.: 524,070

[22] Filed: Aug. 17, 1983

[51] Int. Cl.³ .................. C12N 9/34; C12P 19/20; C12R 1/145
[52] U.S. Cl. .................................... 435/205; 435/96; 435/842
[58] Field of Search .................... 435/205, 96, 842

[56] References Cited

U.S. PATENT DOCUMENTS 4,247,637 1/1981 Tamura et al. .................. 435/96

OTHER PUBLICATIONS

Hockenhull, et al., *Biochem. J.* 39, 102–106, (1945).
Ensley, et al., *J. Gen. Appl. Microbiol.*, 21, 51–59, (1975).

*Primary Examiner*—Lionel M. Shapiro
*Attorney, Agent, or Firm*—Stanley M. Parmerter

[57] ABSTRACT

This invention relates to a glucoamylase enzyme exhibiting thermostability at pH values between 6 and 7 which is derived from a spore-forming, thermophilic, anaerobic bacterium and to a process for its production. The glucoamylase is especially useful for the preparation of glucose-containing syrups from starch.

9 Claims, No Drawings

THERMOSTABLE GLUCOAMYLASE AND METHOD FOR ITS PRODUCTION

FIELD OF THE INVENTION

This invention relates to a novel glucoamylase useful for the hydrolysis of starch and to a method for its production by a species of Clostridium in an anaerobic fermentation.

BACKGROUND OF THE INVENTION

Large quantities of glucose-containing syrups are manufactured by the enzymatic hydrolysis of corn starch. This is generally carried out in two stages. In the first step, the starch is liquefied by treatment with an alpha-amylase enzyme at a pH between 6 and 7. The liquefied starch is then saccharified by means of a glucoamylase enzyme operating at a pH between 4 and 4.5. At present, the commercially-available glucoamylase enzymes used for the saccharification of starch are derived from microorganism of the genera Rhizopus and Aspergillus. These glucoamylases do not exhibit thermostability, particularly in solutions above pH 5.

The glucoamylases in current use are produced by aerobic microorganisms, i.e., those that require oxygen for growth. There are a few reports of glucoamylase being produced by anaerobic organisms. Hockenhull, et al., *Biochem. J.*, 39, 102–106 (1945), found that the anaerobe, *Clostridium acetobutylicum*, produced a glucoamylase. This enzyme displayed a pH optimum at 4.5 Later Ensley, et al., *J. Gen. Appl. Microbiol.*, 21, 51–59 (1975), studied the production of this enzyme and found that it was induced by the presence of glucose in the culture medium.

It would be desirable to hydrolyze starch by conducting the liquefaction and saccharification steps simultaneously in the same reaction mixture. This could be accomplished if a glucoamylase were available that would saccharify the liquefied starch at pH values between 6 and 7 where alpha-amylase is active. In addition, the glucoamylase would have to be sufficiently thermostable at this pH to permit the saccharification reaction to be carried out at a temperature where the reaction rate is fast enough to be useful.

We have now discovered a glucoamylase meeting these requirements that is produced by an anaerobic fermentation reaction.

SUMMARY OF THE INVENTION

In accordance with the present invention, there is provided a glucoamylase enzyme derived from a microorganism selected from the group consisting of Clostridium sp. ATCC No. 39,251, ATCC No. 39,252, mutant strains thereof, or a microorganism incorporating genetic information from said Clostridium sp. microorganisms that codes for the production of a glucoamylase enzyme.

Also provided, in accordance with this invention, is a process for the preparation of a glucoamylase enzyme which comprises selecting a microorganism from the group consisting of Clostridium sp. ATCC No. 39,251, ATCC No. 39,252, mutant strains thereof, or a microorganism incorporating genetic information from said Clostridium sp. microorganisms that codes for the production of a glucoamylase enzyme. Cells of the selected microorganism are cultured in a nutrient medium. Finally, the glucoamylase enzyme is isolated from the culture medium.

Further, in accordance with this invention, is provided a process for hydrolyzing maltodextrin to glucose. This process comprises treating an aqueous solution of the maltodextrin with the glucoamylase enzyme of this invention at a pH of 3.5 to 7.0 for a sufficient time to hydrolyze the maltodextrin to glucose.

DETAILED DESCRIPTION OF THE INVENTION

The glucoamylase of this invention is produced by two new strains of Clostridium that were isolated from mud hot springs in Hveragerdi, Iceland by Dr. Lars G. Ljungdahl and his co-workers at the University of Georgia. They are gram-positive, spore-forming, thermophilic anaerobic bacteria. Dr. Ljungdahl has proposed the same *Clostridium thermoamylolyticum* for these strains which are freely available to the public from the American Type Culture Collection as ATCC No. 39,251 and ATCC No. 39,252.

The microorganisms used for the preparation of the glucoamylase of this invention are grown under anaerobic conditions in a medium which contains a soluble starch or maltodextrin as the carbohydrate source, a yeast extract plus vitamin and mineral solutions. The fermentation is generally conducted between about pH 6 and pH 7. The glucoamylase produced by these microorganisms is found in the fermentation medium along with alpha-amyase. This indicates that the glucoamylase is an extracellular enzyme.

The glucoamylase was purified by removing the cells from the fermentation broth followed by precipitation of extraneous matter with calcium chloride. The mixture of alpha-amylase and glucoamylase was separated by adsorbing the alpha-amylase on granular starch with which it forms a complex. Further purification of the crude glucoamylase was accomplished by ammonium sulfate precipitation followed by several chromatographic separations. The purified enzyme had a molecular weight of about 75,000 as determined by sodium dodecyl sulfate (SDS) polyacrylamide gel electrophoresis.

In the following descriptions of the preparation and properties of the glucoamylase enzyme, all references to parts and percentages are by weight, uless expressly indicated to be otherwise.

Glucoamylase Assay

The substrate used for the assay is a maltodextrin (Maltrin-100 available from the Grain Processing Company, Muscatine, Iowa). 0.1 ml of the enzyme solution was mixed with 0.6 ml of a 5% maltodextrin solution, 0.1 ml of 500 mM sodium acetate solution (pH 5) and water is added to make a total volume of 1 ml. After the mixture is incubated at 60° C. for 30 minutes, the reaction is terminated by immersing the mixture in a boiling water bath for 10 to 20 minutes. Glucose is then determined by the glucose-oxidase method using a glucose analyzer (Yellow Springs Instrument Company, Yellow Springs, Ohio). One glucoamylase unit is defined as the amount of enzyme required to produce 1 gram of glucose in 1 hour under the assay conditions.

alpha-Amylase Assay

The solution to be analyzed is diluted with 0.0025 M calcium chloride solution to give a final concentration of about 0.25 unit of activity per ml. One ml of properly diluted enzyme solution is added to 10 ml of a 1% soluble starch solution containing 0.03 M acetic acid buffer (pH 6.0) and 0.03 M calcium chloride. The reaction is carried out for 10 minutes at 60° C. One ml of the reaction solution is put in a 100-ml graduated flask containing 50 ml of 0.02 N hydrochloric acid, and after adding 3 ml of 0.05% iodine solution thereto, the total volume is made up to 100 ml by the addition of water. The blue color which develops is measured for absorbance at 620 nm. The amount of the enzyme required to decompose 10 mg/starch in 1 minute is defined as 1 unit.

$$1 \text{ unit} = \frac{D_o - D_s}{D_o} \times \frac{50}{10 \times 10} \times \text{(dilution factor)}$$

where, $D_o$ = absorbance of control solution (water is added instead of the enzyme solution)

$D_s$ = absorbance of the reaction solution

Preparation of Glucoamylase

Extracellular glucoamylase enzyme preparations were obtained from two strains of Clostridium sp. ATCC No. 39,251 and ATCC No. 39,252.

Medium preparation and cultivation of samples were carried out using standard anaerobic techniques as described by Hungate, R. E., "A Roll Tube Method for Cultivation of Strict Anaerobes", in *Methods in Microbiology*, edited by J. R. Norris and D. W. Ribbons, Vol. 3B, Academic Press, New York, 1969, pp. 117–132, and by Miller and Wolin, *Appl. Microbiol.*, 27, 985 (1974).

The medium used to produce seed and to maintain the stock culture of the organism had the following composition:

| Seed Medium | |
|---|---|
| Ingredients | Concentration (g/l) |
| Starch (Lintner) | 20 |
| KH$_2$PO$_4$ | 1.5 |
| NH$_4$Cl | 0.5 |
| Na$_2$HPO$_4$.12H$_2$O | 4.2 |
| MgCl$_2$ | 0.18 |
| Yeast Extract | 2.0 |
| Vitamin Solution | 0.5 ml/l |
| Mineral Solution | 50 ml/l |
| Resazurin (0.1%) | 1 ml/l |
| Reducing Solution | 40 ml/l |

| Vitamin Solution | |
|---|---|
| Vitamins | mg/l |
| Biotin | 2 |
| Folic Acid | 2 |
| Pyridoxine.HCl | 10 |
| Riboflavin | 5 |
| Thiamine.HCl | 5 |
| Nicotinic Acid | 5 |
| Pantothenic Acid | 5 |
| B$_{12}$ | 0.1 |
| p-Aminobenzoic Acid | 5 |
| Thioctic Acid | 5 |

| Reducing Solution | |
|---|---|
| Ingredients | Amount |
| NaOH (0.2 N) | 200 ml |
| Na$_2$S.9H$_2$O | 2.5 g |
| Cysteine HCl.H$_2$O | 2.5 g |

| Mineral Solution | |
|---|---|
| Ingredients | mg/100 ml |
| Nitrilotriacetic Acid | 1500 |
| MgSO$_4$.7H$_2$O | 3000 |
| MnSO$_4$.H$_2$O | 500 |
| NaCl | 1000 |
| FeSO$_4$.7H$_2$O | 100 |
| Co(NO$_3$)$_2$.6H$_2$O | 100 |
| CaCl$_2$ | 100 |
| ZnSO$_4$.7H$_2$O | 100 |
| KAl(SO$_4$)$_2$ | 10 |
| H$_3$BO$_3$ | 10 |
| Na$_2$MoO$_4$.2H$_2$O | 10 |
| Na$_2$SeO$_3$ | 1 |

Viable cells could be maintained in the seed medium at room temperature for indefinite periods of time. In order to grow the microorganisms for production of enzyme, sterile seed medium was inoculated with cells and incubated at 56° C. under anaerobic conditions for approximately 30 hours. This produced rapidly-growing cells which were used to inoculate a fermentor. The volume of inoculum was from 1 to 5% of the volume of the growth medium in the fermentor. This medium had the following composition:

| Growth Medium | |
|---|---|
| | g/100 ml |
| Maltrin 100[a] | 1 |
| PROFLO[b] | 5 |
| Prymex[c] | 1 |
| MgSO$_4$.7H$_2$O | 0.5 |
| CaCl$_2$.2H$_2$O | 0.06 |
| MnCl$_2$.2H$_2$O | 0.001 |
| KH$_2$PO$_4$ | 0.13 |
| (NH$_4$)$_2$HPO$_4$ | 1 |

[a] A 10 dextrose equivalent starch hydrolyzate available from the Grain Processing Company, Muscatine, Iowa.
[b] A cottonseed meal available from Traders Oil Mill Company, Fort Worth, Texas.
[c] A yeast extract available from Amber Laboratories, Milwaukee, Wisconsin.

The pH of the medium was adjusted to 6 when the starting strain was ATCC No. 39,251. The pH was adjusted to 7 when the starting strain was ATCC No. 39,252. Production runs were made in a 14-liter fermentor using 10 liters of medium. The yield of extracellular glucoamylase was approximately 0.004 units per ml of fermentation broth.

Purification of the Enzyme

The crude glucoamylase enzyme was purified by the following procedure. The fermentation broth was first filtered through glass wool to remove a gummy insoluble substance. Cells were then removed from the filtrate by means of a Sharples continuous scroll centrifuge, Model 741-24/8R4 (Sharpless Corp., Philadelphia, Pa.) operated at 45 lbs pressure. To the clear supernatant was added sufficient calcium chloride to give a final concentration of about 1.5% w/v and the mixture was stirred for 10 minutes. The bulky precipitate was removed by filtration and discarded. The clear, amber-colored filtrate was then concentrated by an Amicon hollow-fiber (HP-10) concentrator, type AC2, available from the Amicon Crop., Danvers, Mass. Concentration was carried out until the volume was between 500 and 1000 ml before concentrated ammonium hydroxide was added to bring the pH to 6. The addition of ammonium hydroxide caused a second precipitate to form, which was removed by filtration.

Contaminating alpha-amylase enzyme was removed from the filtrate by complexing with granular starch which had been equilibrated with sodium acetate buffer solution containing 50 mM sodium acetate at pH 6 and 5 mM Ca$^{++}$. One gram of starch was used for every 300 units of alpha-amylase enzyme present. The mixture of starch and enzyme solution was stirred gently at room temperature for 60 minutes before the solid was collected by a vacuum filtration. The glucoamylase enzyme in the filtrate was further purified to homogeneity according to the following steps:

1. To the filtrate (910 ml) was added 190.2 g of ammonium sulfate and the mixture was stirred at room temperature for 1 hour. It was then centrifuged at 30,000×g for 20 minutes and the solid was discarded. To the supernatant (1040 ml) was added 331.8 g of ammonium sulfate. The mixture was stirred to complete the precipitation and then the solid, containing the glucoamylase, was separated by centrifugation at 30,000×g for 20 minutes. The solid was dissolved and 300 ml of sodium acetate buffer (50 mM, pH 5.2) and dialyzed at 7° C. against three 2-liter portions of the same buffer during 48 hours.

2. The dialyzed amber-colored enzyme solution was passed through a 2.3×20 cm column filled with DEAE cellulose, Grade DE-52, available from Whatman, Inc., Clifton, N.J. The cellulose column was first equilibrated with sodium acetate buffer (50 mM, pH 5.2). The light yellow fraction which passed through was collected and used for the purification. Approximately 85% of the enzyme activity was recovered in this fraction.

3. The enzyme solution was concentrated to a volume of about 10 ml by means of an Amicon ultrafiltration cell (Amicon Corp., Danvers, Mass.) fitted with a YM 10 membrane of a 10,000 $M_r$ cut. The mixture was clarified by centrifugation at 10,000×g for 10 minutes. Then one-third of the supernatant was loaded on a 1.6×85 cm column of acrylamide agarose gel, Ultrogel AcA 54 (LKB Producter AB, Bromma, Sweden) which had previously been equilibrated with 50 mM sodium acetate buffer containing 100 mM NaCl. The column was eluted with the same buffer at a flow rate of 12 ml/hr. Three ml fractions were collected and checked for glucoamylase activity. The fractions containing enzyme activity were combined and the rest of the supernatant was separated on the Ultrogel column in the same fasion.

4. The combined glucoamylase samples from the gel filtration were diluted with 3 volumes of acetate buffer (50 mM, pH 5) and adsorbed on a 2.3×20 cm column of CM-cellulose, CM-52 available from Whatman, Inc., Clifton, N.J. The enzyme was adsorbed on the top portion of the column forming a yellow band. The column was washed with 200 ml of the acetate buffer before the material was eluted with an NaCl linear gradient (0–0.3 M NaCl in acetate buffer). The enzyme was eluted with 0.14 M NaCl. The fractions with high enzyme activity were combined.

5. The enzyme preparation from Step 4 was concentrated to 3 ml using the Amicon ultrafiltration cell and rechromatographed on the Ultrogel AcA 54 column as described in Step 3 with the collection of three ml fractions. Protein elution was measured by absorption at 280 nm. Four protein peaks were observed. Anaylsis for glucoamylase activity indicated that this enzyme was concentrated in the third peak.

6. The fractions containing the enzyme preparation from Step 5 were dialyzed against 1 liter of acetate buffer (50 mM, pH 4.6) at 7° C. using two changes of buffer during 48 hours. The dialyzed sample was chromatographed on 1.6×20 cm column of CM-Sephadex A-50 previously equilibrated with the acetate buffer at pH 4.6 (CM-Sephadex is available from Pharmacia Fine Chemicals, Ltd., Piscataway, N.J.). The column was washed with 100 ml of the acetate buffer before the enzyme was eluted with 200 ml of buffer containing 0.5 M NaCl. Glucoamylase was eluted in a sharp peak. The protein content of the enzyme-containing solution was determined by the method of Lowry, et al., *J. Biol. Chem.*, 193, 265–275 (1951), using bovine serum albumin as a standard. A summary of purification procedure is given in Table I. By this procedure, the enzyme was purified 320-fold to give a purified sample with a specific activity of 1.6 units/mg protein. Chromatofocusing indicated that the glucoamylase had an isoelectric point at pH 5.6.

TABLE I

PURIFICATION OF GLUCOAMYLASE FROM ATCC NO. 39,251

| Procedure | Volume (ml) | Unit Per ml | Unit Per mg Protein | Yield (%) |
|---|---|---|---|---|
| Culture Supernatant | 13,500 | 0.0037 | 0.0055 | 100 |
| Ultrafiltration | 910 | 0.0496 | 0.0077 | 89.8 |
| Starch-Affinity | 910 | 0.0454 | 0.0075 | 82.2 |
| 35–80% (NH4)2SO4 | 325 | 0.1100 | 0.0270 | 71.2 |
| DE-52 Column | 490 | 0.0620 | 0.0302 | 60.5 |
| Ultrogel AcA 54 | 174 | 0.1380 | 0.0418 | 47.8 |
| CM-52 Column | 81 | 0.1648 | 0.1555 | 26.6 |
| Ultrogel AcA 54 | 30 | 0.3133 | 0.7813 | 18.7 |
| CM-Sephadex | 24.8 | 0.2100 | 1.628 | 10.4 |

Molecular Weight of the Enzyme

The purified glucoamylase was determined to be homogeneous by its migration as a single protein band when subject to polyacrylamide gel electrophoresis either in the presence or absence of SDS. The molecular weight of the enzyme was estimated to be 75,000 by SDS-polyacrylamide gel electrophoresis according to the procedure of Laemmli, *Nature*, 227, 680–685 (1970). This is somewhat smaller than the molecular weight of 100,000 reported for the glucoamylase derived from the fungi *Aspergillus niger*, Pazur, J. H., "Analysis of Gluocoamylase", in *Methods in Enzymology*, Vol. 28, edited by V. Ginsburg, Academic Press, New York, 1972, pp. 931–934, and the molecular weight of 87,000 given for the glucoamylase from *Aspergillus oryzae*, Saha, et al., *Starch*, 31, 307–314 (1979).

Thermostability of the Enzyme

The thermostability of the purified glucoamylase was compared with that of two other known glucoamylases. The purified enzyme was diluted with sodium acetate buffer (100 mM, of the desired pH) to give a protein concentration of 12 μg/ml. The enzyme solutions were incubated at 70° C. At appropriate time intervals (usually 5, 10, 20, 30, 60 and 120 minutes), vials were removed and immediately cooled in an ice bath. Residual enzyme activity was assayed at pH 5 and 60° C. using the standard assay procedure. The half-life of the enzyme was calculated by linear regression. Results given in Table II indicate that the enzyme of the present invention shows superior stability at 70° C. and pH 5 or 6 over the glucoamylases produced by *Talaromyces duponti* and *Aspergillus niger*. It has a half-life of over 3 hours at pH 6 and 70° C.

TABLE II

THERMOSTABILITY OF GLUCOAMYLASE AT 70° C.

| Enzyme | Half-Life (minutes) at | | |
|---|---|---|---|
| | pH 4.3 | pH 5 | pH 6 |
| Glucoamylase of this Invention | <5 | 68 | 215 |
| T. duponti Glucoamylase[a] | 14 | 24 | 11 |
| A. niger Glucoamylase[b] | <5 | 18 | 11 |

[a] U.S. Pat. No. 4,247,637.
[b] A commercial enzyme available from the Enzyme Development Corp., 2 Penn Plaza, New York, N.Y.

pH Effect on the Enzyme

The glucoamylase enzyme activity was analyzed by the standard procedure except that the pH of the substrate was varied from 3.5 to 8.5 using 100 mM buffer solutions of the following compositions: citrate (pH 3.5), acetate (pH 4 to 6), HEPES (pH 6.5 to 7.5) and TRIS-acetate (pH 8-8.5). The relative activities at various pHs given below indicate that the enzyme shows maximum activity at pH 5.0.

| pH | Percent of Maximum Activity |
|---|---|
| 3.5 | 65 |
| 4.0 | 73 |
| 4.5 | 87 |
| 5.0 | 100 |
| 5.5 | 96 |
| 6.0 | 93 |
| 6.5 | 86 |
| 7.0 | 75 |
| 7.5 | 10 |
| 8.0 | 5 |
| 8.5 | 2 |

Temperature Optimum for the Enzyme

The effect of the reaction temperature on the purified enzyme was determined by performing the standard (pH 5) assay for glucoamylase activity at various temperatures. At this pH, the optimum temperature for action of the enzyme was 70°-75° C.

Substrate Specificity of the Enzyme

The enzyme hydrolyzed maltodextrin and soluble starch. It also hydrolyzed maltose but the rate of hydrolysis was less than half the rate of hydrolysis of maltodextrin. The enzyme did not hydrolyze the dextran from *L. mesenteroides* which contains principally 1,6-linkage between the glucose units.

The foregoing tests demonstrate that there is provided by this invention a glucoamylase enzyme that hydrolyzes starch at pH values between 6 and 7. Furthermore, the glucoamylase is sufficiently thermostable in this pH range to permit its use to hydrolyze starch at a temperature where the reaction rate is fast enough to be useful. While the invention has been described with specific embodiments thereof, it will be understood that it is capable of further modification and adaptations or variations as apparent to those skilled in the enzyme and starch hydrolysis art.

What is claimed is:

1. A glucoamylase enzyme derived from a *Clostridium thermoamylolyticum* microorganism, said enzyme having a molecular weight of about 75,000±3,000 as determined by SDS-polyacrylamide gel electrophoresis, having a half-life of greater than 3 hours at pH 6 and 70° C., having a maximum glucoamylase activity at a pH of about 5.0, and having a maximum glucoamylase activity at pH 5 at a temperature of about 70°-75° C.

2. A glucoamylase enzyme derived from a microorganism selected from the group consisting of Clostridium sp. ATCC No. 39,251, ATCC No. 39,252, and mutant strains thereof, said glucoamylase having a half-life greater than 3 hours at pH 6 and 70° C.

3. The enzyme of claim 2 further characterized as having a molecular weight of about 75,000±3,000 as determined by SDS-polyacrylamide gel electrophoresis.

4. The enzyme of claim 2 further characterized as having a maximum glucoamylase activity at a pH of about 5.0.

5. The enzyme of claim 2 further characterized as having a maximum glucoamylase activity at pH 5 at a temperature of about 70°-75° C.

6. A process for producing a glucoamylase enzyme having a molecular weight of about 75,000±3,000 as determined by SDS-polyacrylamide gel electrophoresis, having a half-life of greater than 3 hours at pH 6 and 70° C., having a maximum glucoamylase activity at a pH of about 5.0, and having a maximum glucoamylase activity at pH 5 at a temperature of about 70°-75° C., which comprises culturing cells of a strain of *Clostridium thermoamylolyticum* in a nutrient medium and then isolating the glucoamylase enzyme from the medium.

7. A process for producing a glucoamylase enzyme which comprises selecting a microorganism from the group consisting of Clostridium sp. ATCC No. 39,251, ATCC No. 39,252, and mutant strains thereof, culturing cells of the selected microorganism in a nutrient medium and then isolating the glucoamylase enzyme from the medium.

8. A process for hydrolyzing maltodextrin to glucose comprising treating an aqueous solution of the maltodextrin with the glucoamylase enzyme of claim 1 at a pH of 3.5 to 7.0 for a sufficient time to hydrolyze the maltodextrin to glucose.

9. The process of claim 8 wherein the hydrolysis is conducted at a temperature in the range of from about 45° C. to about 80° C. at a pH of about 4.0 to about 6.5.